(12) United States Patent
Han et al.

(10) Patent No.: US 6,651,010 B1
(45) Date of Patent: Nov. 18, 2003

(54) VECTOR-BASED METHOD FOR VISUALIZING SECONDARY STRUCTURE OF RNA MOLECULES

(75) Inventors: Kyungsook Han, Ichon-si (KR); Dohyung Kim, Inchon-si (KR); Hong-Jin Kim, Inchon-si (KR)

(73) Assignee: INHA University Foundation, Inchon-si (KR)

( * ) Notice: Subject to any disclaimer, the term of this patent is extended or adjusted under 35 U.S.C. 154(b) by 0 days.

(21) Appl. No.: 09/210,305

(22) Filed: Dec. 11, 1998

(30) Foreign Application Priority Data

Oct. 13, 1998 (KR) ............................................. 98-42655

(51) Int. Cl.[7] .............................................. G06F 19/00
(52) U.S. Cl. ..................................................... 702/27
(58) Field of Search ............................. 702/27, 19, 20; 364/496; 703/11

(56) References Cited

U.S. PATENT DOCUMENTS 4,461,619 A * 7/1984 Hendry et al. ............... 434/295
5,888,738 A * 3/1999 Hendry ........................... 435/6

OTHER PUBLICATIONS

Han et al. "A vector–based method for drawing RNA Secondary Structure," Bioinformatics 15(4), 286–297, 1999.*

Chetouani et al., Nucleic Acids Research, vol. 25, No. 17, pp. 3514–3522, 1997.*

Hogeweg et al., Nucleic Acids Research, vol. 12, No. 1, pp. 67–74, 1984.*

CABIOS, vol. 9, No. 5, 1993, pp. 551–561 for Automatic Display of RNA Secondary Structures.

CABIOS, vol. 12, No. 3, 1996, pp. 205–211 for Visualization of RNA Secondary Structures Using Highly Parallel Computers.

* cited by examiner

Primary Examiner—Ardin H. Marschel
(74) Attorney, Agent, or Firm—Bachman & LaPointe, P.C.

(57) ABSTRACT

There is disclosed a method for visualizing secondary structures of RNA molecules, by which nearly overlap-free polygonal displays of RNA secondary structures are produced with minimal distortion to structural elements, with minimal search for positioning them, and with minimal user intervention. While vector and vector space are used to determine the direction and space of a structural element, two heuristics are adopted for the task of searching for the space and direction of structural elements. With the aid of the two heuristics, loops are positioned in decreasing order of their sizes and a helix is positioned, depending on the position of its adjacent loop which has been positioned. In consideration of both a potentially open and wide vector space and an allowed vector space, a structural element is positioned.

6 Claims, 15 Drawing Sheets

FIG. I

```
GAGUGACAACGCG
--(((----)))-
```

|  | Format | Example |
|---|---|---|
| Data Format I | $ \<starting number\> \<basequence\><br>% \<starting number\> \<matching parentheses and minus symbols\> | $ 1 CAGgUCUCUCUGGUUUUAGACCAGA<br>% 1 -----(((((((((-----))))))<br>$ 26 UcUGAG<br>% 26 ---))) |
| Data Format II | \<base sequence\><br>\<matchin parentheses and minus symbols\> | CAGgUCUCUCUGGUUUUAGACCAGAUcUGAG<br>-----(((((((((-----))))))---))) |

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
          (A) LENGTH: 96 base pairs
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 1:

```
CGGGCCCCUG CCGCCUGCAA GUCGAAAUUG CGCUGUGCUC CUGUGCUACG GCCUGUGGCU      60

GGACUGCCUG CUGCUGCCCA ACUGGCUGGC AAGAUG                                96
```

(2) INFORMATION FOR SEQ ID NO: 2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 2:

```
GAGUGACAAC GCG                                                    13
```

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 3:

```
CAGGUCUCUC UGGUUUUAGA CCAGAUCUGA G                                31
```

(2) INFORMATION FOR SEQ ID NO: 4:

(i) SEQUENCE CHARACTERISTICS:
        (A) LENGTH: 89 base pairs
        (B) TYPE: nucleic acid
        (C) STRANDEDNESS: double
        (D) TOPOLOGY: linear (ii) MOLECULE TYPE: oligonucleotide (xi) SEQUENCE DESCRIPTION: SEQ ID NO: 4:

```
CCAAGUCCUA AGUGGACCUC UCCUUAAUGG GAGCUAGCGG AUGAAGUGCA CUGGAGCCGC    60
UGGGAACUAA UUUGAUUAGU UUUGGAGUA                                     89
```

(2) INFORMATION FOR SEQ ID NO: 5:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

```
AUUGGGCGUA AAGCGUCUGU AGGUGGCUCG UAAAGUCUAA UGUCAAAUAC CAGGGCUCAA    60
CCUUGGACCG GCAUUGGAUA CUCACGAGCU UGAGUACGGU AGGGGCAGAG GGAAUUCCAU   120
GUGGAGCGGU GAAAUGCGUA GAGAUAUGGA GGAACACCAG UGGCGAAGGC GCUCUGUCGG   180
GCCGAAACUG ACACUGAGAG AGGAAAGCUG GGGGAGCGAA UAGGAUUAGA UACCCUAGUA   240
GUCCCAGCCG UAAACUAUGG AGACUAAGUG CUGCCGCAAG CAGUGCUGUA GCUAACGCGU   300
UAAGUCUCCC GCCUGGGGAG UAUGCUCGCA AGAGUGAAAC UCA                     343
```

(2) INFORMATION FOR SEQ ID NO: 6:

(i) SEQUENCE CHARACTERISTICS:
        (A) LENGTH: 414 base pairs
        (B) TYPE: nucleic acid -continued

```
            (C) STRANDEDNESS: single
            (D) TOPOLOGY: linear (ii) MOLECULE TYPE: oligonucleotide (xi) SEQUENCE DESCRIPTION: SEQ ID NO: 6:

GAAAUAGCAA UAUUUACCUU UGGAGGGAAA AGUUAUCAGG CAUGCACCUG GUAGCUAGUC        60

UUUAAACCAA UAGAUUGCAU CGGUUUAAAA GGCAAGACCG UCAAAUUGCG GGAAAGGGGU       120

CAACAGCCGU UCAGUACCAA GUCUCAGGGG AAACUUUGAG AUGGCCUUGC AAAGGGUAUG       180

GUAAUAAGCU GACGGACAUG GUCCUAACCA CGCAGCCAAG UCCUAAGUCA ACAGAUCUUC       240

UGUUGAUAUG GAUGCAGUUC ACAGACUAAA UGUCGGUCGG GGAAGAUGUA UUCUUCUCAU       300

AAGAUAUAGU CGGACCUCUC CUUAAUGGGA GCUAGCGGAU GAAGUGAUGC AACACUGGAG       360

CCGCUGGGAA CUAAUUUGUA UGCGAAAGUA UAUUGAUUAG UUUUGGAGUA CUCG             414

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 7:

GAAAUAGCAA UAUUUACCUU UGGAGGGAAA                                         30

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 8:

GAAAUAGCAA UAUUUACCUU UGGAGG                                             26
```

VECTOR-BASED METHOD FOR VISUALIZING SECONDARY STRUCTURE OF RNA MOLECULES

BACKGROUND OF THE INVENTION

1. Field of the Invention

The present invention relates to a vector-based method for visualizing secondary structures of RNA molecules. More particularly, the present invention is concerned with an improvement in producing overlap-free polygonal displays of secondary structures with minimal distortion to structural elements, with minimal search for positioning them and with minimal user intervention.

2. Description of the Prior Art

In order to better understand the background of the invention, the basic concept and technical terminologies used herein will be illustrated with reference to FIG. 1 which shows the structural elements of an RNA molecule.

A structural element refers to either a double-stranded part (i.e., helix) or a single-stranded part such as an internal loop, bulge loop, multiple loop, or dangling end, as shown in FIG. 1. A structural element consists of one or more structural units, each of which is a contiguous segment of a base sequence. The double-stranded part, called helix or stem, is formed by the existence of two or more contiguous base pairs in an RNA molecule. The internal loop is a protruded part as a result of the failure of pairing bases in both strands while the bulge loop is a protruded part which results from the failure of pairing bases in one strand. The multiple loop is referred to a stretch or stretches of unpaired bases through which two or more helices are jointed. As for the dangling end, it is an unpaired part at the start or end of the base sequence.

Adjacent helices to a loop v mean helices directly connected to v. Adjacent loops to a loop v include all loops connected to v via a single helix. A seed loop of a loop v is an adjacent loop to v, which has already been positioned. A regular secondary structure is one having no bulge loop, dangling end, or helices directly adjacent to each other.

There are several representation methods for RNA secondary structure, including polygonal display, mountain, and circles and domes. They are exemplified by the drawings of FIGS. 2b to 2e with respect to the secondary structure of FIG. 2a.

In essence, the secondary structure of RNA is a topological structure, which depends utterly on the connectivity relation of the constituting bases, rather than a geometric structure. One of the aims of representing the structure in graphical forms is to facilitate the comparison and evaluation of RNA secondary structure by sight. It is virtually impossible to evaluate the secondary structure of an RNA molecule which consists of a large number of bases, unless it is properly visualized. Since evaluating and comparing an RNA secondary structure is accomplished by validating the connectivity relation of the bases, it is a useful representation method by which a clear and compact graphic form free of structural element overlap, is produced. For intuitional recognition of the whole topology of the second structure, the graphic form produced is required not to be under distortion (e.g., bending, contorting or resizing of structural elements) as best as possible.

Most drawing programs of RNA secondary structures first produce graphical forms with overlapping structural elements, and then remove the overlap by deforming (bending, contorting and/or resizing) the structural elements with user intervention (Devereux, J., Haeberli, P., and Smithies, O. (1984) A comprehensive set of sequence analysis programs for the Vax. Nucleic Acids Res., 12, 387–395; Shapiro, B. A., Maizel, J., Lipkin, L. E., Currey, K., and Whitney, C. (1984) Generating non-overlapping displays of nucleic acid secondary structure. Nucleic Acids Res., 12, 75–88) or by an iterative process or backtracking of programs (Bruccoleri, R., E., and Heinrich, G. (1988) An improved algorithm for nucleic acid secondary structure display. CABIOS, 4, 167–173; Lapalme, G., Cedergren, R. J., and Sankoff, D. (1982) An algorithm for the display of nucleic acid secondary structure. Nucleic Acids Res., 10, 8351–8356; Stüber, K. (1985) Visualization of nucleic acid sequence structural information. CABIOS, 1, 35–42; Muller, G., Muller, G., Gaspin, C. Etienne, A., and Westhof, E. (1993) Automatic display of RNA secondary structures. CABIOS, 9, 551–561; Perochon-Dorisse, J., Chetouani, F., Aurel, S., Iscolo, N., and Michot, B. (1995) RNA_d2: a computer program for editing and display of RNA secondary structure. CABIOS, 11, 101–109).

Where the overlap of structural elements is removed with programs, the elements are deformed according to rules. The deforming rules introduced, however, are applied indiscriminately to all structural elements, so the resulting secondary structures are likely to be distorted (e.g., particular structural elements are too bent or contorted).

In addition, since the visualizing programs require high computational power, they often run on a mainframe or workstation level computer, which is not easily available to RNA researchers.

A recent algorithm (Nakaya et al., (1996) Visualization of RNA secondary structures using highly parallel computers. CABIOS, 12, 205–211) generates a polygonal display in O(NlogN) time by applying an O(NlogN) force-calculation algorithm, originally developed by Barnes and Hut (1986, A hierarchical O(NlogN) force-calculation algorithm. Nature, 324, 446–449). However, their algorithm has been implemented disadvantageously using a parallel programming language on a parallel computer.

In brief, many methods for visualizing the secondary structures of RNA molecules have been reported, inclusive of, for example, Chetouani, F., Monestié, P., Thébault, P., Gaspin, C., and Michot, B. (1997) ESSA: an integrated and interactive computer tool for analyzing RNA secondary structure. Nucleic Acids Res., 25, 3514–3522;

Hogeweg, P. and Hesper, B. (1984) Energy directed folding of RNA sequences. Nucleic Acids Res., 12, 67–74;

Matzura, O. and Wennborg, A. (1996) RNA draw: an integrated program for RNA secondary structure calculation and analysis under 32-bit Microsoft Windows. CABIOS, 12, 247–249;

Nussinov, R. Pieczenik, R., Griggs, G. and Kleitman, J. (1978) Algorithms for loop matching. SIAM J. Appl. Math., 35, 68–82; and Osterburg, G. and Sommer, R. (1981) Computer support of DNA sequence analysis. Comput. Progr. Biomed., 13, 101–109.

these are found to show at least one of the following disadvantages: full automation is not settled in the visualizing process, so there is much room for user intervention; structural elements are frequently deformed, which makes it difficult to recognize the overall topology; high performance computers like parallel computers are needed; and an exponential time for automatically producing an overlap-free display is taken due to backtracking.

Therefore, to avoid the above problems, active research has been and continues to be directed to the development of methods for visualizing secondary structures of RNA molecules, by which clear and compact graphic products can be obtained fast and at a low cost.

SUMMARY OF THE INVENTION

The objective of the present invention is to overcome the above problems encountered in prior arts and to provide a method for visualizing secondary structures of RNA molecules, by which the structures can be drawn as a polygonal display.

Another objective of the present invention is to provide the visualizing method by which the polygonal display can be produced with minimal overlap.

It is a further objective of the present invention to provide the visualizing method in which distortion level to avoid overlap of structural elements is kept as little as possible.

It is still a further objective of the present invention to provide the visualizing method with minimal user intervention.

It is still another objective of the present invention to provide the visualizing method which can be implemented in the Microsoft Window operating system on IBM compatible personal computers.

In accordance with the present invention, the above objectives could be accomplished by a provision of a method for visualizing an RNA secondary structure, which uses vector and vector space to determine the position of a structural element and which comprises the steps of regularizing a secondary structure, building data structures, determining positioning priority, and positioning and drawing structural elements.

In the step of regularizing a secondary structure, the secondary structure is transformed into a regular one by introducing artificial bases so that it does not contain any bulge loop, dangling end, or helices directly adjacent to each other. A regularized secondary structure is stored in a data structure called an organization object.

The building data structures step is composed of identifying structural elements from the organization object and constructing the data structures of the secondary structure object and the draw list object for each of the identified structural elements.

The positioning priority is determined by first computing the sizes of all loops and determining the positioning priorities of all structural elements, including helices. A data structure called a priority queue stores these priorities.

As for the step of positioning and drawing structural elements, it comprises computing open and allowed vector spaces and a feasible vector, starting from a structural element with the highest drawing priority. A structural element shall be positioned in the direction of the feasible vector. For each positioned structural element, the coordinates of its constituting bases are computed and they are displayed.

BRIEF DESCRIPTION OF THE DRAWINGS

The above and other objects and aspects of the invention will become apparent from the following description of embodiments with reference to the accompanying drawings in which:

FIG. 1 shows structural elements of an RNA secondary structure, wherein FIG. 1 is represented by SEQ. ID NO: 1;

FIGS. 2a to 2e show various representation types for an RNA secondary structure, wherein FIGS. 2a to 2e are represented by SEQ. ID NO: 2;

FIG. 9 shows the input data formats used in the present invention, wherein FIG. 9 is represented by SEQ. ID NO: 3;

FIG. 10 shows data structures of a secondary structure object, draw list object and organization object;

FIG. 15 shows a secondary structure of C. reinhardii chloroplast 16s-like rRNA, drawn by the method of the present invention, wherein FIG. 15 is represented by SEQ. ID NO: 5; and FIG. 16 shows a secondary structure of Tetrahymena intervening sequence, drawn by the method of the present invention, wherein FIG. 16 is represented by SEQ. ID NO: 6.

DETAILED DESCRIPTION OF THE INVENTION

Figure 2A:
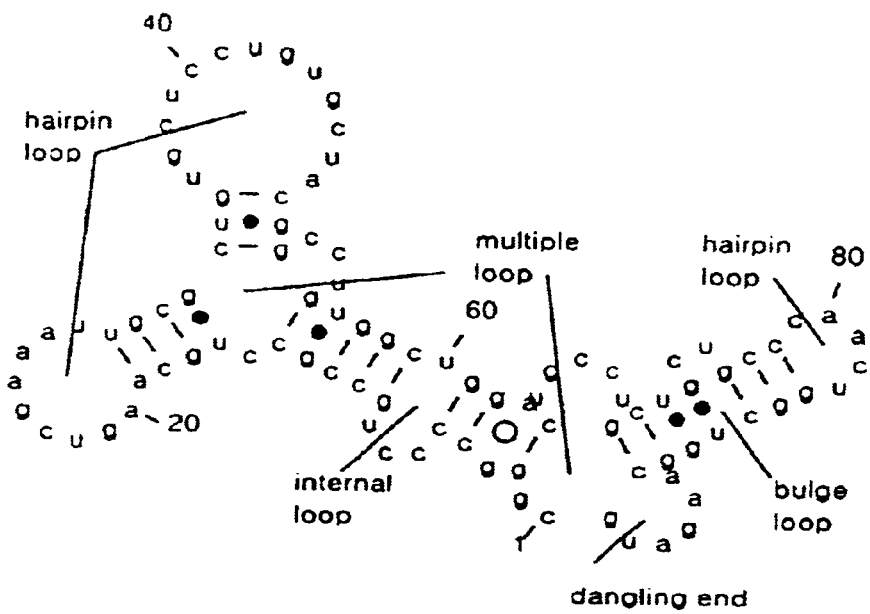
Figure 2B:
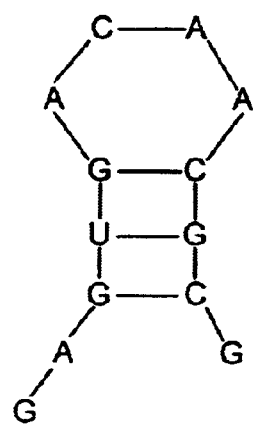
Figure 2C:
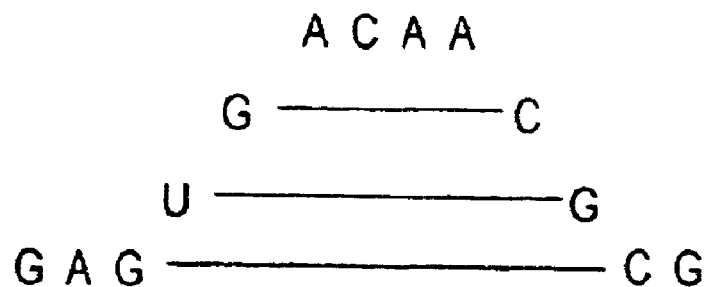
Figure 2D:
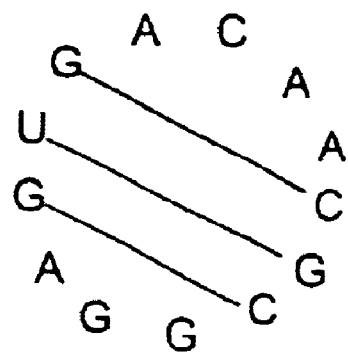
Figure 2E:
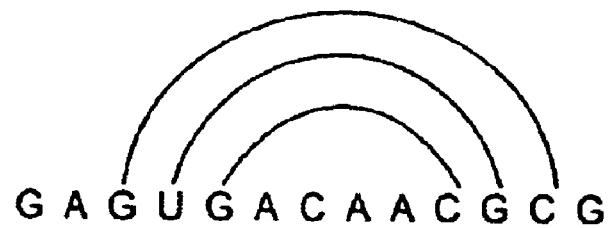
Figure 3:
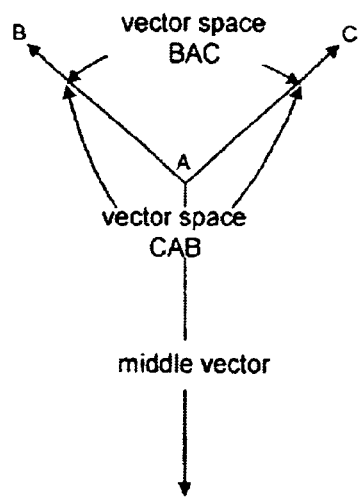
FIG. 3 shows vector space and a middle vector which indicates an intended one among two vector spaces.

In visualizing a secondary structure of an RNA molecule, a vector is used to designate the direction of a structural element to be positioned. In order to help understand the invention, a description will be given of vector space and middle vector, below. Referring to FIG. 3, vector spaces and a middle vector are shown. A vector has a direction and a magnitude, but no fixed position in space. Two non-identical vectors partition the plane into two unbounded wedge regions, as shown in FIG. 3. A vector space is used here to designate the unbounded wedge region lying between two vectors starting at a common point; so, ABAC denotes a vector space formed by sweeping a vector AB clockwise until it reaches AC, while ACAB denotes the complementary vector space.

Since two non-identical vectors define two vector spaces, a middle vector is defined to indicate an intended vector space. An open vector space refers to a potentially open and wide space, which is not obstructed by other structural elements. The open vector space is an ideal region for a structural element to be located. However, it is not always possible to position a loop in an open vector space due to the helices adjacent to its seed loop and the bases of the seed loop. Therefore, an allowed vector space is defined as a realistic vector space in which a loop can be located. In consideration of both the open and allowed vector spaces of a loop, the loop is actually positioned in the direction of a feasible vector. The detailed methods for computing the vectors and the vector spaces defined above shall be discussed later.

The application of the preferred embodiments of the present invention is best understood with reference to the accompanying drawings.

The invention is to produce a polygonal display of an RNA secondary structure with minimal overlap and distortion of structural elements, with minimal search for positioning them, and with minimal user intervention. As described above, vector and vector space are used to determine the direction and space of a structural element. The only distortion operation allowed to avoid overlapping is the rotation of helices.

For this, two heuristics are used. The first heuristic is concerned with ordering structural elements while the second one with placing them in space. First, loops are positioned in decreasing order of their sizes. The position of a helix is dependent on that of its adjacent loop, which has been positioned. Second, a structural element is positioned based on both open and allowed vector spaces of it.

In approaching the present invention, a loop is positioned such that its center is located in the extended line containing its adjacent helix. Since the size of a loop or helix is proportional to the number of bases constituting the structural element, its size is not changed in an attempt to resolve overlap. Instead, a rotation is made on a helix and its adjacent loop. With this method, overlap can be avoided without resizing or distorting the earlier structural elements.

Figure 4:
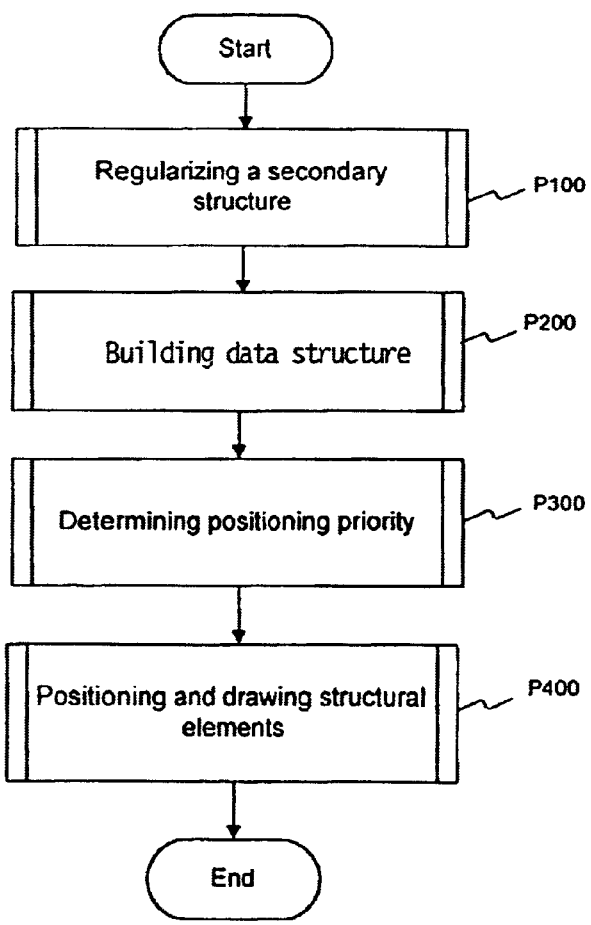
FIG. 4 is a flow chart showing the visualization of an RNA secondary structure, according to the present invention.

With reference to FIG. 4, there is a flow chart showing the visualizing process for RNA secondary structures, according to the present invention. As seen, the process is composed largely of four steps: regularizing a secondary structure (P100); building data structures (P200); determining positioning priority (P300); and positioning and drawing structural elements (P400), each will be described in great detail, below.

Figure 5:
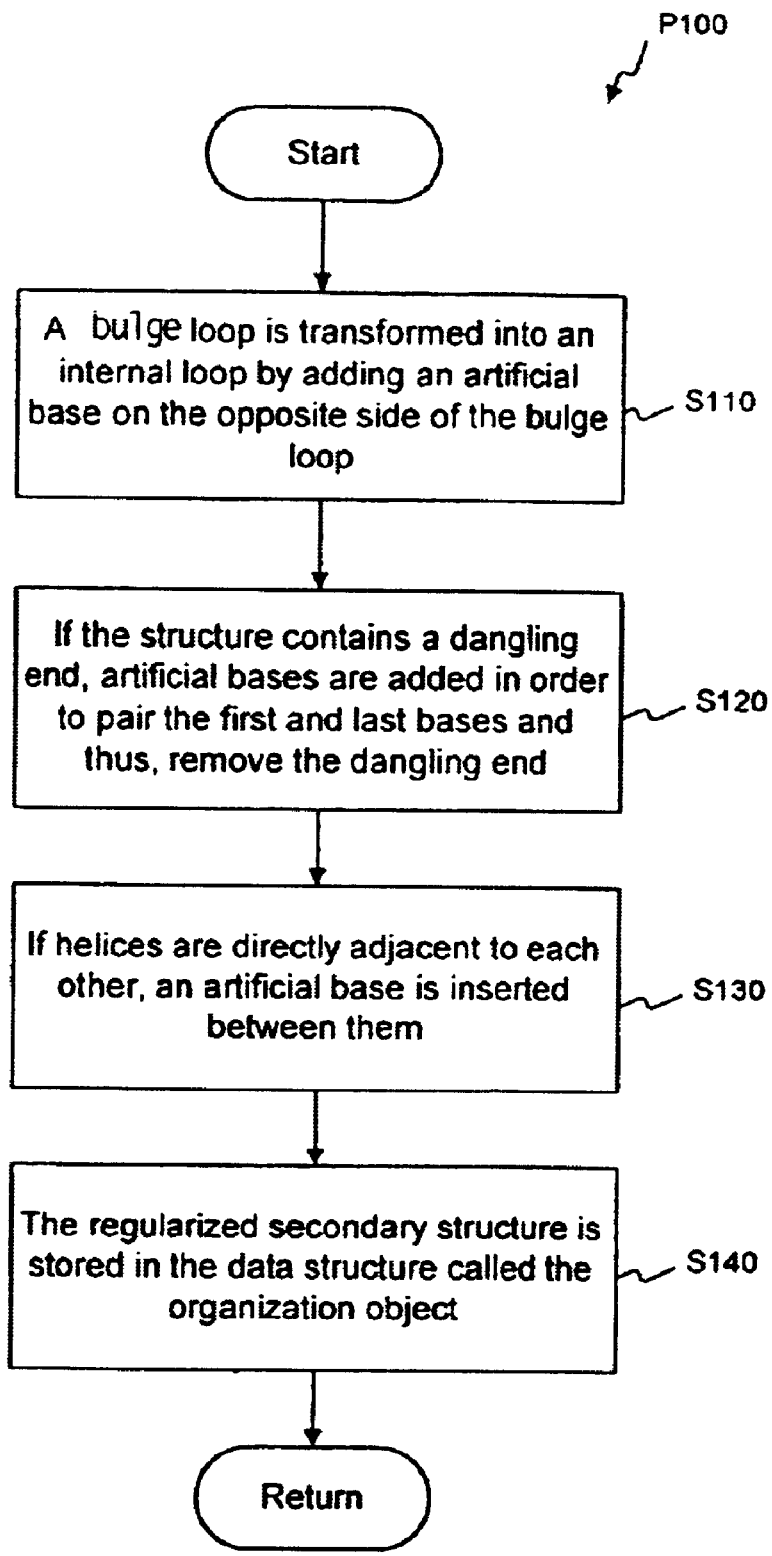
FIG. 5 is a flow chart showing the regularizing of a secondary structure, according to the present invention.

First, the step of regularizing a secondary structure is accomplished by following the flow shown in FIG. 5. In order to generalize the updating process of a data structure, the secondary structure represented in a text form is pre-processed as in the following. The input data as used herein are represented as either of the formats of FIG. 9. Neither of them is limited in line length. The data for an RNA secondary structure can be input through a keyboard or read from a file stored. The input data in both formats are editable, later, with appearance on a monitor during the visualization.

Figures 9, 10:
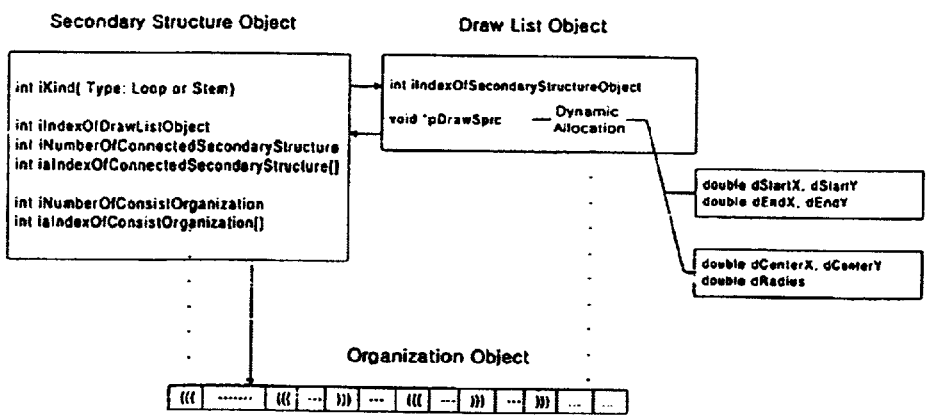

Returning to the Preprocessing,

1. A bulge loop is transformed into an internal loop by adding an artificial base on the opposite side of the bulge loop (S110). For example, "((((( - - - - ))) - - - )))" is transformed into "((( - ((( - - - - ))) - - - )))".
2. If the structure contains a dangling end, artificial bases are added in order to pair the first and last bases and thus, remove the dangling end (S120). For example, " - - - ((( - - - - )))" or " - - - ((( - - - - ))) - - - " is transformed into "((( - - - ((( - - - - ))) - - - )))".
3. If helices are directly adjacent to each other, an artificial base is inserted between them (S130). For example, "((( - - - - )))((( - - - - )))" is transformed into "((( - - - - ))) - ((( - - - - )))". The artificial bases introduced in this step are marked, and not actually drawn in the last step of the invention.
4. The regularized secondary structure is stored in the data structure called the organization object, in which the secondary structure is partitioned into structural units (S140). The data structures used in the present invention are shown in FIG. 10.

Figure 6:
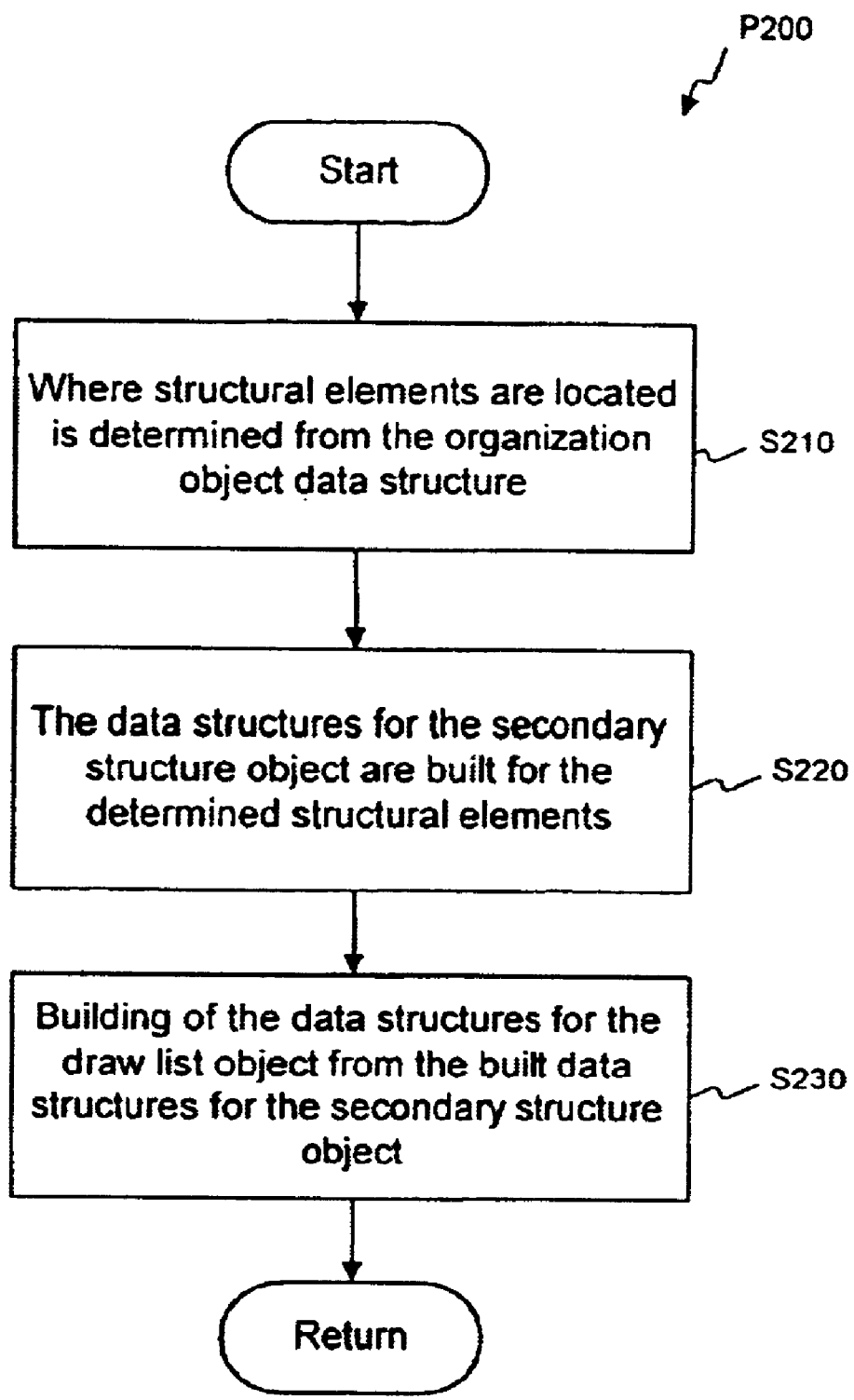
FIG. 6 is a flow chart showing the building of data structures, according to the present invention.

The building step of data structures is stepwise depicted in FIG. 6.

This step is performed by identifying structural elements from the secondary structure regularized above and building data structures corresponding to the secondary structure object and draw list object for each of the identified structural elements. First, the location of structural elements (helix structure or loop) in the base sequence is determined from the organization object constructed above (S210). The data structures for the secondary structure object are built for the determined structural elements (S220), followed by the building of the data structures for the draw list object from the built data structures for the secondary structure object (S230).

In more detail, structural elements such as loops and helices are identified from the regularized secondary structure and the data structures are initialized for each of the identified structural elements. They are the secondary structure object (SSO) and draw list object (DLO). While the SSO contains display device-independent information, the DLO contains device-dependent information such as the coordinates of objects. The SSO contains the indexes to the structural units of the organization object forming the structural element, indexes to the adjacent structural element, and the index to the DLO corresponding to the structural element. The DLO contains the index to the SSO, and the position of a structural element; center position and radius are maintained for a loop, while start and end positions are maintained for a helix.

Figure 7:
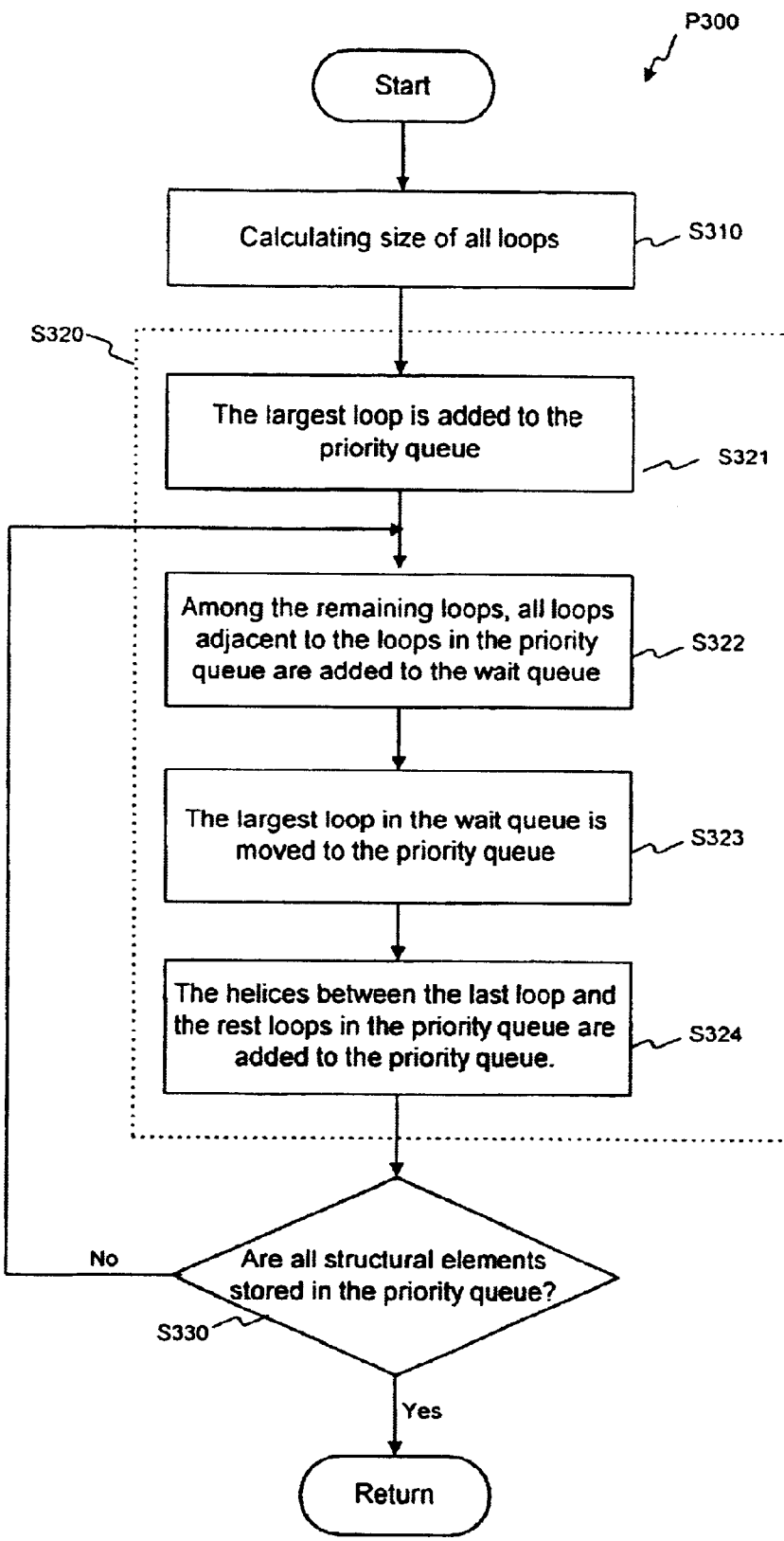
FIG. 7 is a flow chart showing the determining of positioning priority, according to the present invention.

Referring to FIG. 7, there is a flow chart to show the determining step of positioning priority. As seen, the sizes of all loops are calculated and positioning priorities for all structural elements including helix structures are determined, followed by the storage of the data structure called priority queue.

In detail, considering the adjacency of structural elements and the radii of loops, placing order of the elements in the DLO is determined. When computing a loop radius, it is assumed that each base is a circle with a diameter 1 and that the distance between the centers of adjacent bases is 2. Artificial bases introduced in the regularizing step are also included in computing the radius of a loop (S310). The determination process of the drawing priority can be described as below. First, the largest loop is added to the priority queue (S321). Second, among the remaining loops, all loops adjacent to the loops in the priority queue are added to the wait queue (S322). Third, the largest loop in the wait queue is moved to the priority queue (S323). Fourth, the helices between the last loop and the rest of the loops in the priority queue are added to the priority queue (S324). Fifth, the steps 2, 3, and 4 are repeated until all structural elements are stored in the priority queue. After the determination process is completed, structural elements are stored in a priority queue in decreasing order of positioning priority.

Figure 8:
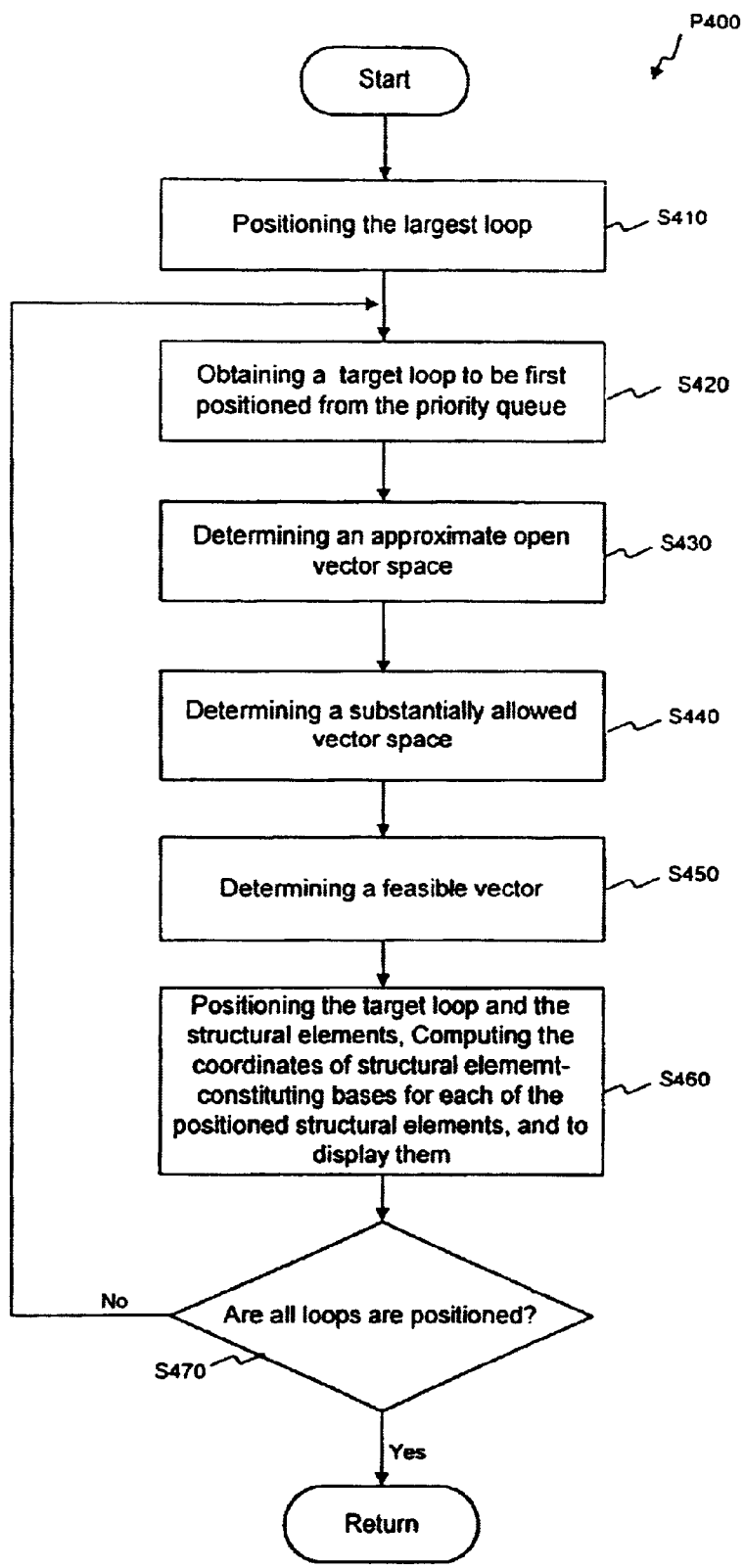
FIG. 8 is a flow chart showing the positioning and drawing of structural elements, according to the present invention.

FIG. 8 illustrates the positioning and drawing step of structural elements. As seen, starting from a structural element with the highest drawing priority, open and allowed vector spaces and a feasible vector are computed. A structural element is positioned in the direction of the feasible vector. Then, for each positioned structural element, the coordinates of its constituting bases are computed and they are displayed.

For the task of searching for the space and direction of structural elements, two heuristics are used that minimize the overlap of the structural elements without increasing search effort and distortion level to avoid the overlap. The first heuristic is concerned with ordering structural elements to be placed and has already been employed in determining the drawing priority in the previous step. The second heuristic is concerned with placing them in the proper space and employed in finding out the open vector space to be described later. The first thing to be done in this step is to position the largest loop first (S410). The position of a helix is automatically determined from that of a loop adjacent to it. Then, a target loop to be first positioned from the priority queue, is obtained (S420), after which an approximate open vector space is determined as a prework for positioning the target loop in the direction where an open and wide space exists (S430). It is for efficiency that an approximate open vector, instead of an exact open vector space, is found.

An approximate open vector is determined as follows. The left vector of an open vector space for a target loop is a vector starting at the seed loop of the target loop and directing toward the last loop visited in the traverse of the rightmost loop connected to the seed loop. The right vector of an open vector space is a vector starting at the seed loop and directing toward the last loop visited in the traverse of the leftmost loop connected to the seed loop. The open vector space is an unbounded wedge region between the left and right vectors.

Figure 11:
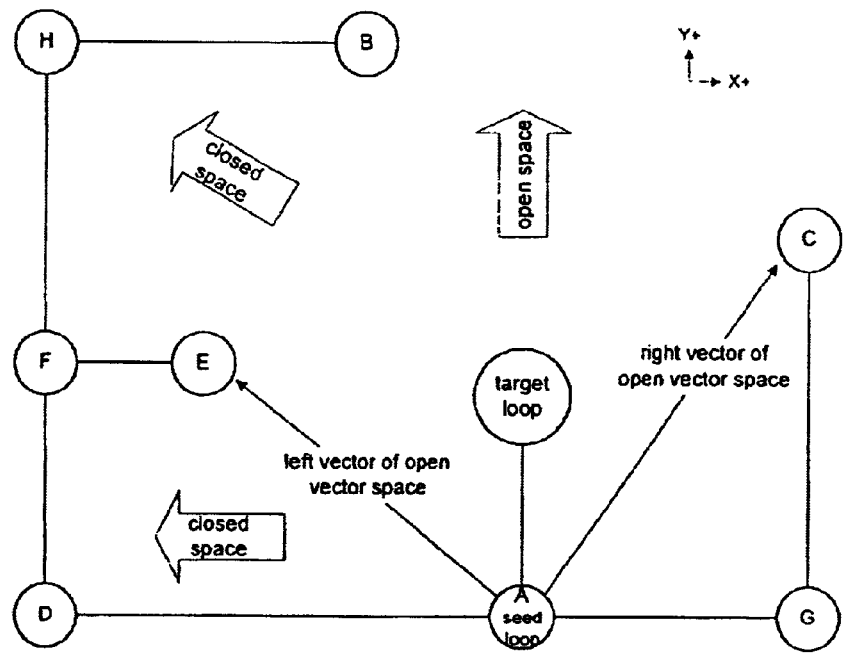
FIG. 11 shows a process of determining an approximate open vector space.

Referring to FIG. 11, an approximate open vector space in which to position a target loop is determined as follows. To find the left vector of an open vector space, loop D is first visited. The only unvisited loop adjacent to D is F, so F is visited. Unvisited loops adjacent to F are E and H. Among them, E is the rightmost loop, so it is visited. There are no unvisited loops adjacent to E. Thus, E becomes the end point of the left vector of the open vector space, and AE become the left vector. The right vector is found in a similar manner, except that the leftmost loop is chosen at each step of a traverse. AC becomes the right vector of the open vector space. Thus, $\Lambda$EAC is the open vector space for the target loop. The reason why $\Lambda$EAC is found instead of $\Lambda$BAC is that an approximate open vector space is found for efficiency. To find such an exact open vector space, all vectors identified must be tested for intersection, and this testing increases the complexity of the algorithm.

Now, turning to FIG. 8, the fourth is to determine a substantially allowed vector space if the open vector for the target loop is determined (S440). As mentioned earlier, a middle vector indicates an intended vector space. The angle between the left and the middle vector of a vector space is less than $\pi$, so is the angle between the right and the middle vector. Thus, the middle vector of a vector space can be computed by algebraic operations on the left and right vectors of the vector space.

If LeftVector lies to the left of RightVector,

Middlevector=(LeftVector+RightVector)/2

Else

MiddleVector=INVERSE(LeftVector+RightVector)/2

In the above equation, whether or not the left vector lies to the left of the right vector can be determined as follows.

dValueOfDecision=VectorRight.dVector*(VectorLeft.dEndY−VectorRight.dEndY)−VectorRight.dVectorY*(VectorLeft.dEndX−VectorRight.dEndX)

if (dValueOfDecision>0)
    LeftVector lies to the left of RightVector.
else if (dValueOfDecision<0)
    Left Vector lies to the right of RightVector.

Figure 12A:
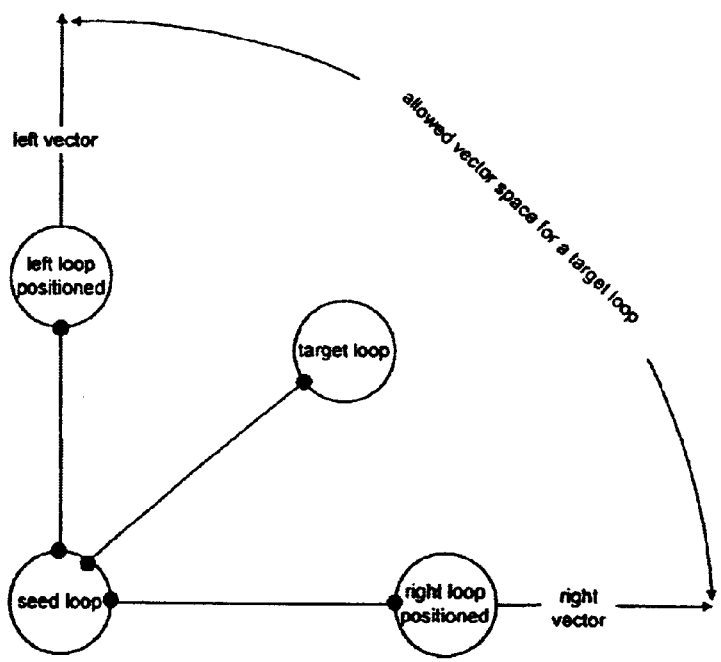
FIGS. 12a and 12b show a process of determining an allowed open vector space.
Figure 12B:
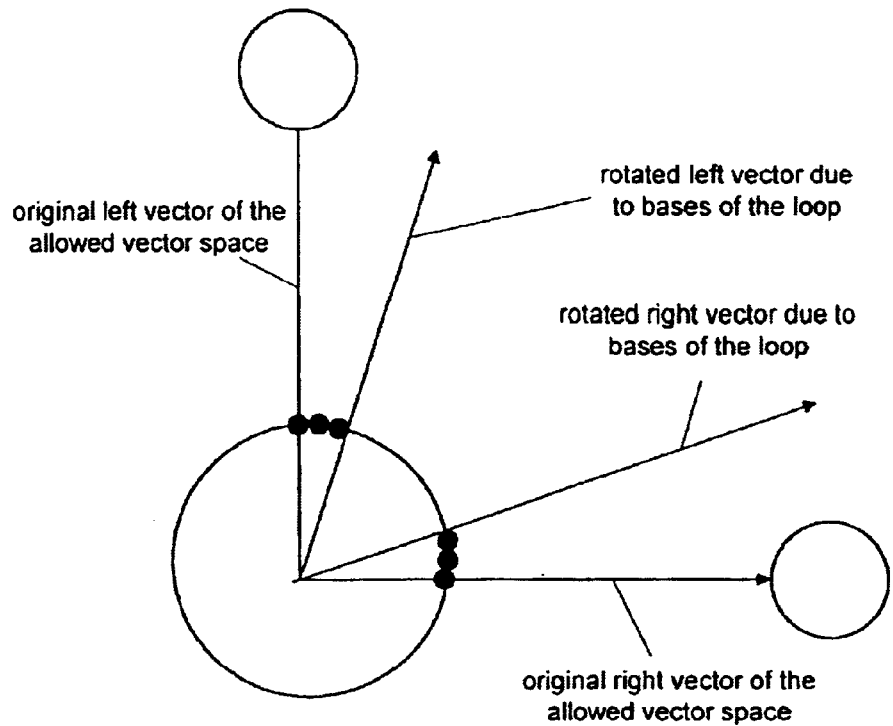

The middle vector of an open vector space is an ideal direction for a target loop to be put. However, positioning a target loop in such a direction may not be possible if the space for a target loop is limited by adjacent helices which have been positioned already (See FIG. 12*a*). In addition, the bases of the seed loop can further restrict the space for a target loop (See FIG. 12*b*). Thus, an allowed vector space is defined, which represents a realistic vector space in which a loop can be located.

Figure 13A:
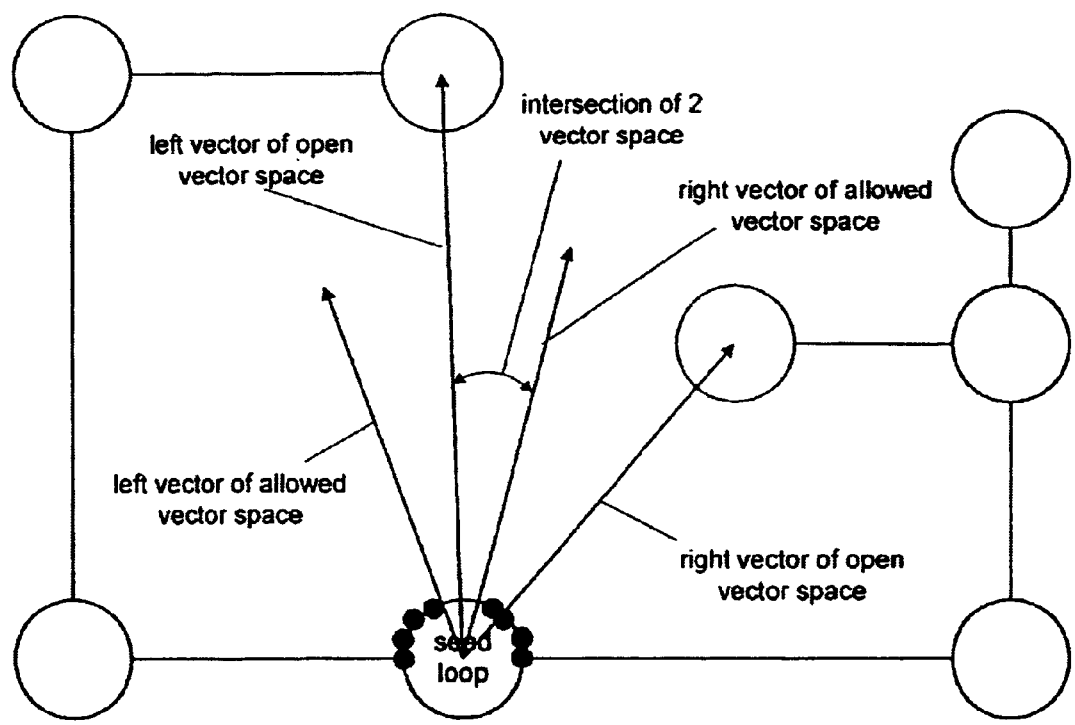
FIGS. 13a to 13d show a process of determining a feasible vector for a target loop.

In FIG. 8, the fifth is to determine a feasible vector (S450). Based on both the open vector space and the allowed vector space for a target loop, the direction is determined in which the target loop shall be actually positioned, as shown in FIG. 13*a*. The feasible vector represents this direction.

Two cases are distinguished.

Figure 13B:
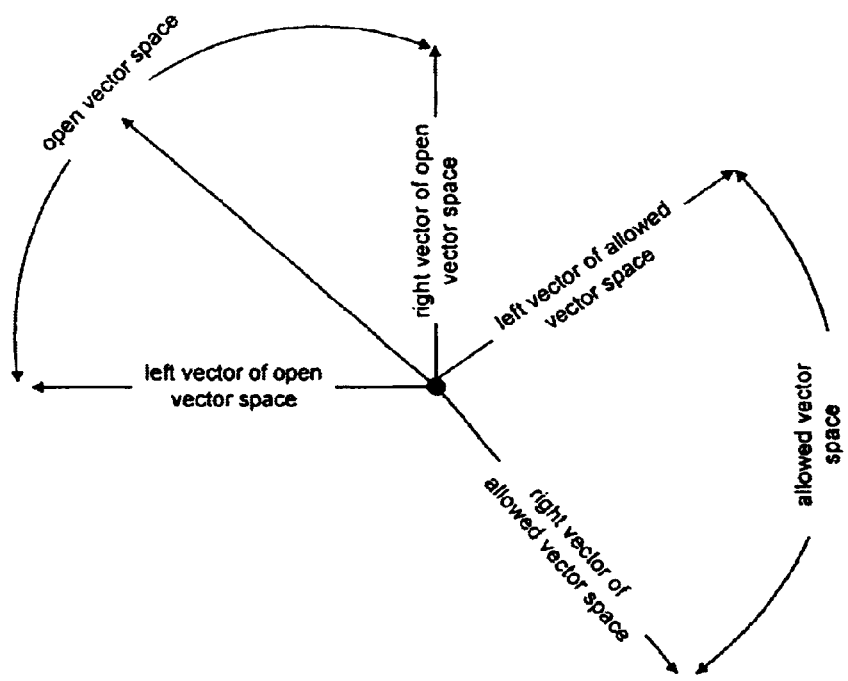

Case 1: The allowed vector space contains the middle vector of the open vector space, as shown in FIG. 13*b*. The feasible vector is set to the middle vector of the open vector space.

Figure 13C:
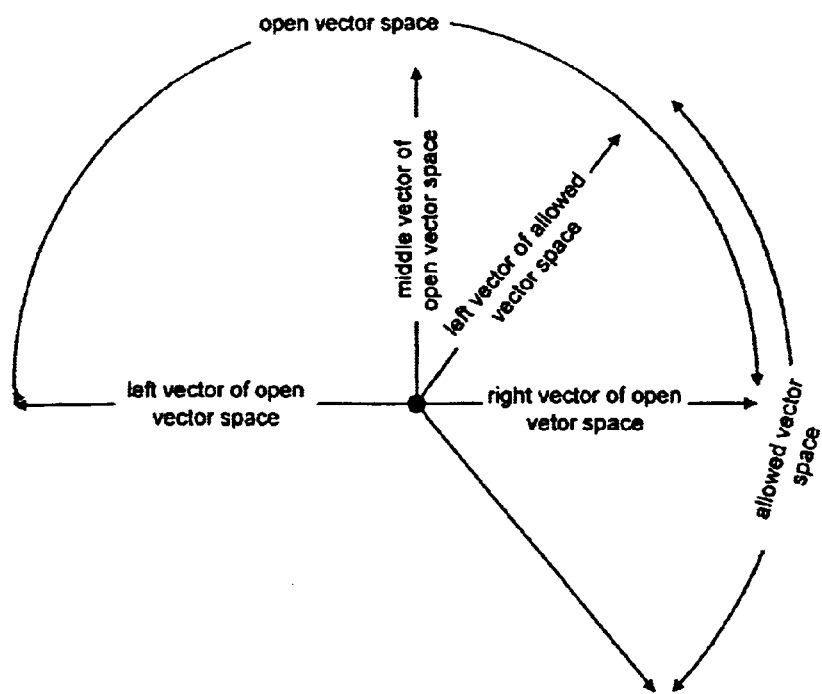
Figure 13D:
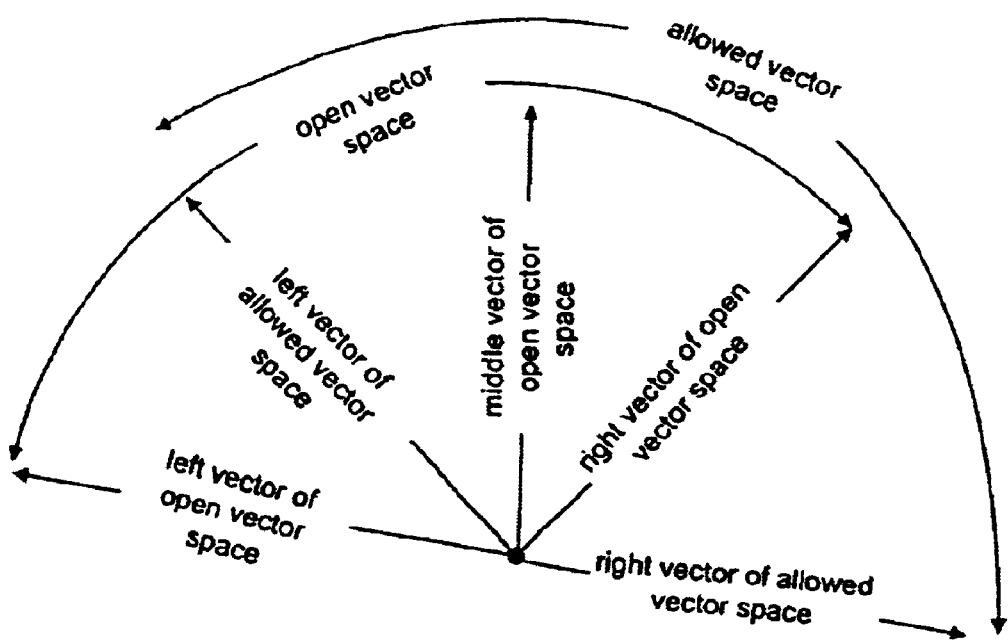

Case 2: The allowed vector space does not contain the middle vector of an open vector space, as shown in FIGS. 13*c* and 13*d*. Out of the left and right vectors of the allowed vector space, the one closer to the middle vector of the open vector space is selected as the feasible vector.

Returning to FIG. 8, the sixth is to position the target loop and the structural elements in the direction of the feasible vector, to compute the coordinates of structural element-constituting bases for each of the positioned structural elements, and to display them (S460).

For each vector, the start position, direction, and magnitude are internally maintained. If any of these components is changed, remaining components of the vector are automatically changed. When the feasible vector for a target loop is determined, the center position of the target loop is computed as follows.

VectorFeasible.dMagnitude=LoopSeed.dRadius+StemTarget.dLength+LoopTarget.dRadius LoopTarget.dCenterX=VectorFeasible.dStartX+VectorFeasible.dDirectionX LoopTarget.dCenterY=VectorFeasible.dStartY+VectorFeasible.dDirectionY The start and end position of a target helix are computed as follows.

VectorFeasible.dMagnitude=StemTarget.dLength+LoopSeed.dRadius

StemTarget.dEndX=VectorFeasible.dStartX+VectorFeasible.dDirectionX

StemTarget.dEndY=VectorFeasible.dStartY+VectorFeasible.dDirectionY

VectorFeasible.dMagnitude=LoopSeed.dRadius

StemTarget.dStartX=VectorFeasible.dStartX+VectorFeasible.dDirectionX

StemTarget.dStartY=VectorFeasible.dStartY+VectorFeasible.dDriectionY

Once the start and end positions of a helix, and the center and radius of a loop have been computed, displaying the bases of them on a display device is relatively straightforward. The steps S420 to S460 are repeated untill all loops and structural elements are positioned and displayed. The procedure for positioning and drawing structural elements mentioned can be summarized as follows.
1. Delete from the DLO a target loop and a target helix. The target helix is one that is adjacent to the target loop and its seed loop, if any.
2. Compute the open and allowed vector spaces for the target loop.
3. Based on the open and allowed vector spaces, compute the feasible vector for the target loop.
4. Position the target loop in the direction of the feasible vector.
5. Position the target helix in the direction of the feasible vector.
6. Display the positioned structural elements.

Figure 14:
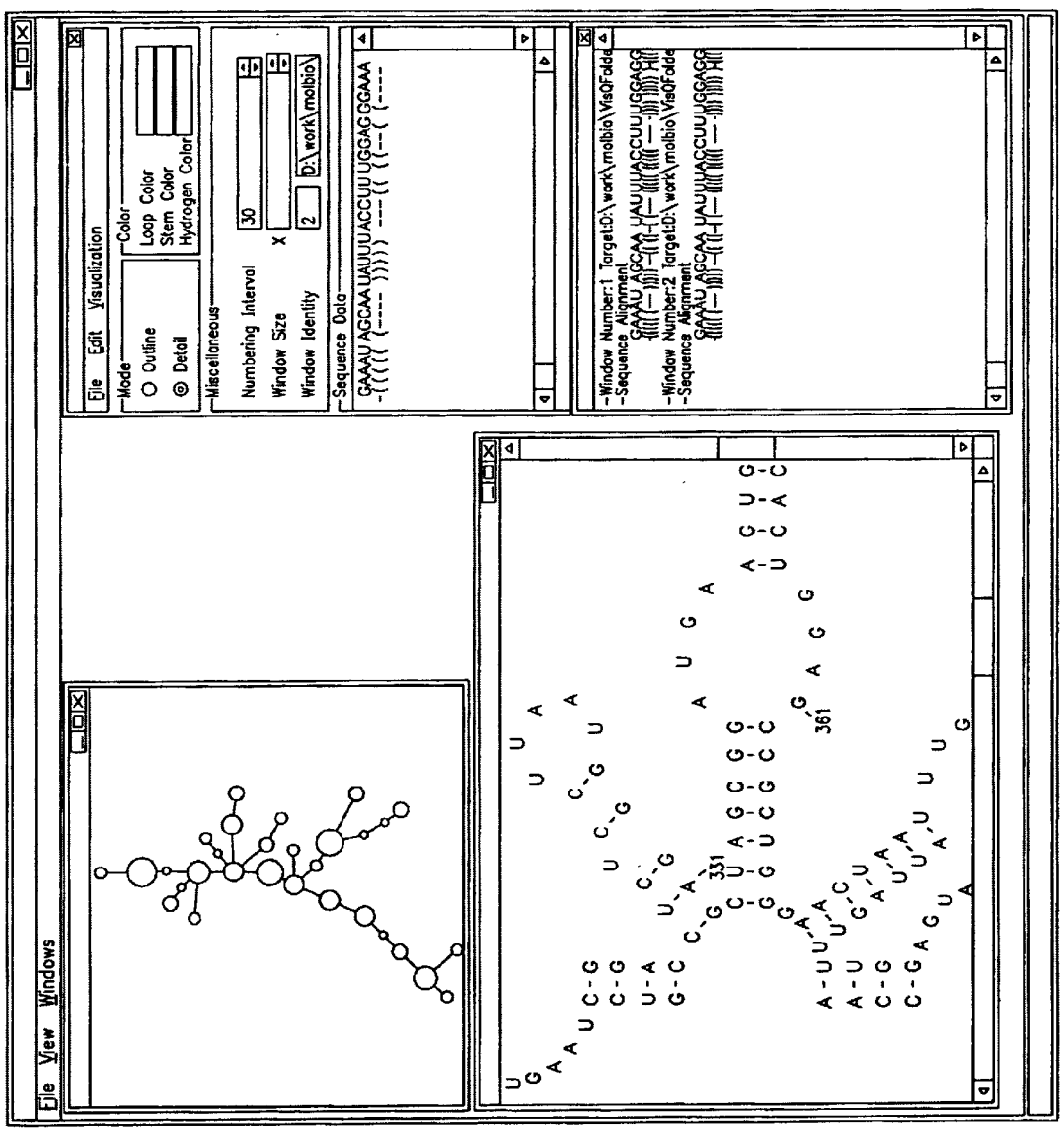
FIG. 14 shows output forms generated by the method of the present invention, wherein the lower left hand window is represented by SEQ. ID NO: 4, the upper right hand window is represented by SEQ. ID NO: 7 and lower right hand window is represented by SEQ. ID NO: 8.

As output, two kinds of drawings for RNA secondary structures, i.e., standard polygonal view and outline view, are produced, as shown in FIG. 14. In the standard polygonal view, the RNA secondary structure is displayed in the form where bases, symbols between paired bases, and base numbering are specified. The outline view displays the structure in the form of a backbone in which loops are replaced by circles and helices by line segments.

Since the program of the invention is implemented using Multiple Document Interfaces (MDI), it is possible to generate several structure models for different RNA molecules without leaving a session according to the present invention. Each generated model is assigned to a separate window which has its own window identity assigned by the user for later reference. This facility is convenient particularly when comparing several models to search for structural motifs.

The following are other convenient features of the user interface of the invention:
1. A history window is produced, which keeps a record of operations.
2. The secondary structure data can be read either from a keyboard or from a file in flexible form. Data given in either form can be edited later.
3. The secondary structure data can be shown all the time while they are being visualized.

Below will be described the complexity according to the visualization of the secondary structure. There are $O(n)$ structural elements in an RNA secondary structure with n bases. The first step of regularizing a secondary structure takes $O(n^2)$ time since it requires $O(n)$ time for each structural element in the worst case. In the second step, data structures are built in $O(n)$ time. The third step of determining drawing priority uses $O(n^2)$ time since $O(n)$ time is required for each structural element. The final step of placing and drawing structural elements also takes $O(n^2)$ time. Thus, the method of the invention has an overall $O(n^2)$ time bound.

The visualizing method of an RNA secondary structure according to the present invention can be run on IBM-PC compatible computers with the Windows 95 operating system. Modification of a system-dependent part only is enough to port the method of the present invention on other systems.

Figure 15:
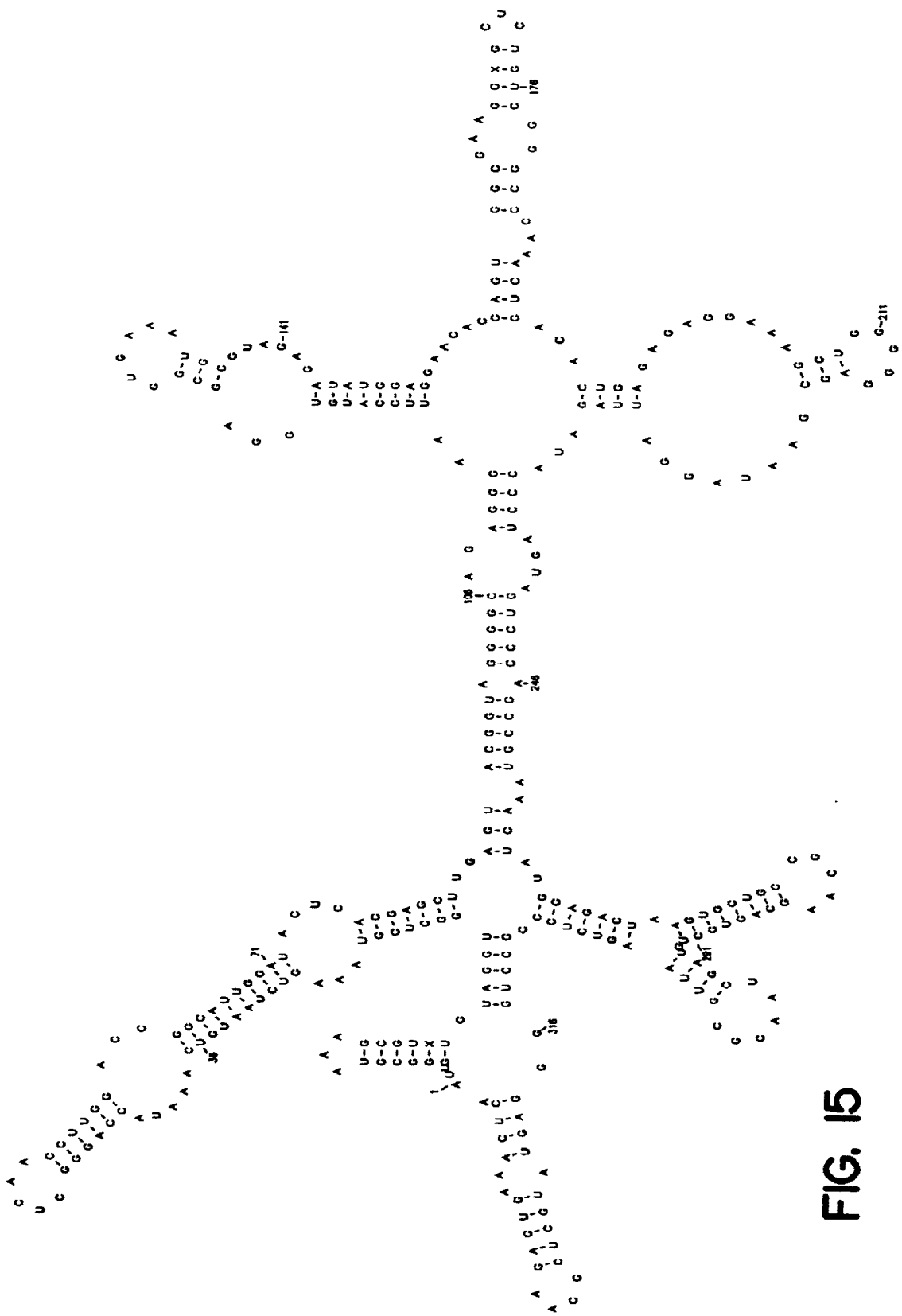
Figure 16:
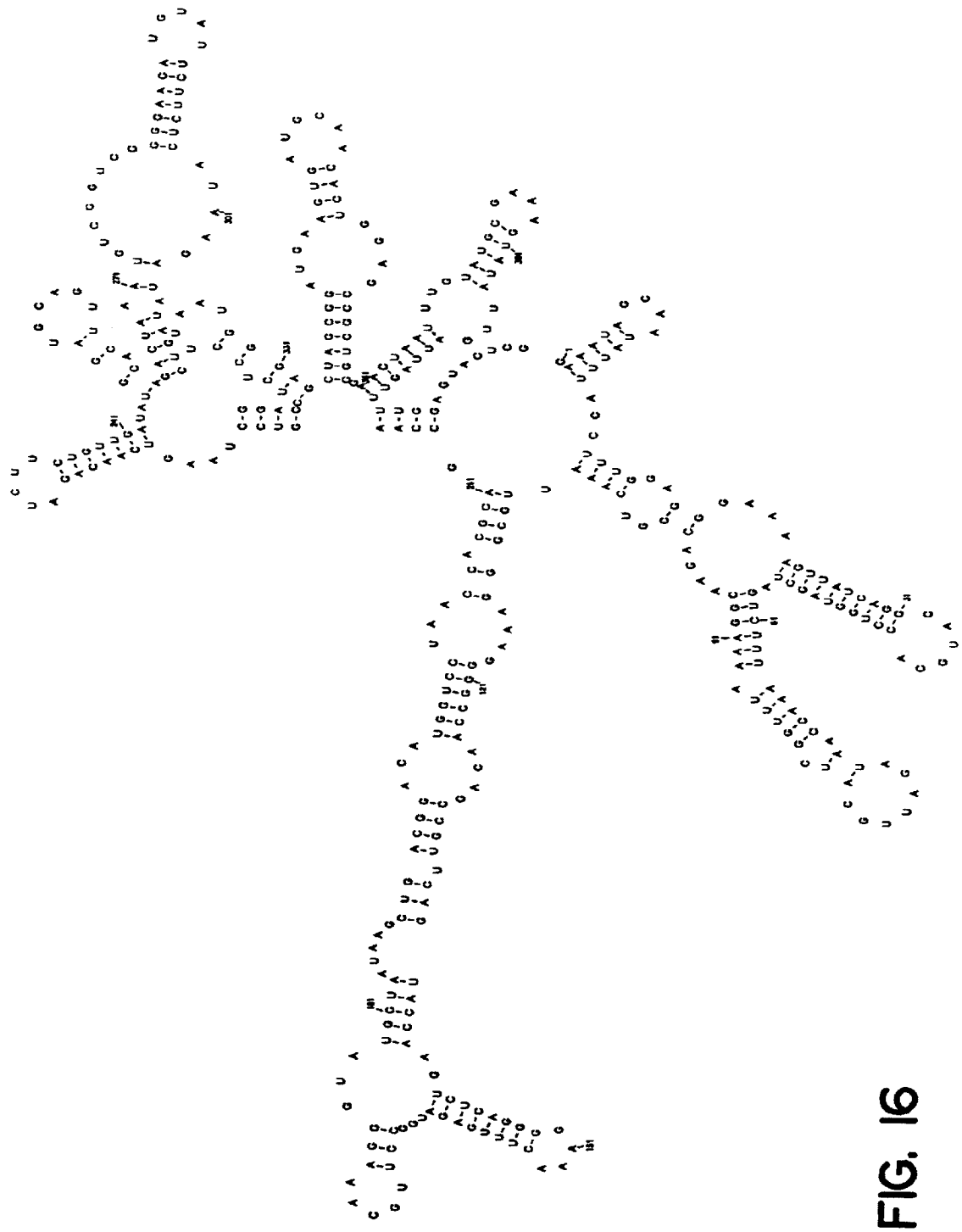

Examples of secondary structure models generated by the visualizing method of the invention are given in FIGS. 15 and 16. The total response time, measured by Zprofiler (Baars, A (1998) Zprofiler, a Delphi component for high-resolution timing (version 2.20) published electronically on the Internet), for drawing the secondary structure for domain 2 of C. reinhardii chloroplast 16S like rRNA (see FIG. 15) is ca. 340 ms on a Pentium MMX 200 Mhz processor. The secondary structure data of the C. reinhardii chloroplast 16S like rRNA was obtained from the prediction of MFOLD (Zuker et al., 1991). The total response time for drawing the secondary structure of Tetrahymena intervening sequence (Cech, T. R., et al., (1983) Secondary structure of the Tetrahymena ribosomal RNA intervening sequence: Structural homology with fungal mitochondrial intervening sequences. *Proc. Natl. Acad. Sci. USA*, 80, 3903–3907) presented in FIG. 16 is ca. 390 ms. According to the result of Zprofiler, large part of the response time is ascribed to creating a bitmap and drawing, instead of computation for positioning. Both FIGS. 15 and 16 are original drawings generated by the invention with no user intervention for modification.

As described hereinbefore, overlap-free polygonal displays of RNA secondary structures can be automatically produced with minimal distortion to structural elements and with minimal user intervention, according to the present invention. In addition, the present invention can visualize the secondary structures of RNA molecules of any type and may be run on relatively low cost computers such as personal computers.

What is claimed is:

1. A method for visualizing a secondary structure of a single-stranded RNA molecule, which uses a vector and vector space to determine the direction and space of structural elements and which includes the steps of:

regularizing said secondary structure, wherein the regularizing said secondary structure step is carried out by transforming the secondary structure into a regular secondary structure through the introduction of at least one artificial base so that the structure does not contain any bulge loop, dangling end, or helices directly adjacent to each other, and then storing the regularized secondary structure in a data structure which plays the role of an organization object;

building data structures, wherein the building data structure step is implemented by identifying structural elements from the organization object and constructing data structures of a secondary structure object and a draw list object for each of the identified structural elements;

determining positioning priority, wherein said determining positioning priority step is comprised of computing the sizes of all loops in the constructed data structure, determining the positioning priorities of all structural elements including helices, and storing the determined priorities in a data structure, which is a priority queue; and positioning and drawing structural elements, wherein the positioning and drawing structural elements step is carried out by computing open and allowed vector spaces and a feasible vector with the starting point being a structural element with the highest drawing priority, positioning a structural element in the direction of the feasible vector, computing the coordinates of structural element-constituting bases for each of the positioned structural elements, and displaying them.

2. A method as set forth in claim 1, wherein the regularizing a secondary structure step is carried out by transforming a bulge loop into an internal loop by adding an artificial base on the opposite side of the bulge loop when said secondary structure of an RNA molecule contains a bulge loop, adding artificial bases in order to pair the first and last bases and thus, removing the dangling end when the structure contains a dangling end, and inserting an artificial base between helices when the helices are directly adjacent to each other.

3. A method as set forth in claim 1, wherein said secondary structure object contains device-independent information including the indexes to the structural units of the organization object forming the structural elements, indexes to adjacent structural elements and the index to the draw list object corresponding to the structural elements, and said draw list object contains device-dependent information including the index to the secondary structure object and the position of a structural element.

4. A method as set forth in claim 1, wherein said priorities are determined in such a way that the largest loop is added to the priority queue, all remaining loops adjacent to the loops in the priority queue are added to a wait queue, the largest loop in the wait queue is moved to the priority queue, and the helices between the last loop and the rest of the loops in the priority queue are added to the priority queue while the process is repeated until all structural elements are stored in the priority queue.

5. A method as set forth in claim 1, wherein said open vector space during positioning and drawing of structural elements is obtained from an approximate open vector space instead of an exact open vector space, said and approximate open vector space is determined as an unbounded wedge region between a left and a right vector of the open vector space for a target loop, said left vector being a vector starting at a seed loop for the target loop and directing toward the last loop visited in the traverse of the rightmost loop connected to the seed loop, and said right vector being a vector starting at the seed loop and directing toward the last loop visited in the traverse of the leftmost loop connected to the seed loop.

6. A method as set forth in claim 1, wherein, when the allowed vector space during positioning and drawing of structural elements contains a middle vector of the open vector space, the feasible vector is set to the middle vector of the open vector space and, when the allowed vector space does not contain the middle vector of an open vector space, the one closer to the middle vector of the open vector space is selected as the feasible vector, out of the left and right vectors of the allowed vector space.

* * * * *